United States Patent
Miller

(10) Patent No.: US 9,345,830 B2
(45) Date of Patent: May 24, 2016

(54) PUMP AND MONITOR FOR IV PRESSURE BAG INFUSERS

(71) Applicant: Sprout Medical, Inc., Danville, CA (US)

(72) Inventor: Paul Joseph Miller, Alameda, CA (US)

(73) Assignee: Sprout Medical, Inc., Danville, CA (US)

( * ) Notice: Subject to any disclaimer, the term of this patent is extended or adjusted under 35 U.S.C. 154(b) by 321 days.

(21) Appl. No.: 13/767,795

(22) Filed: Feb. 14, 2013

(65) Prior Publication Data

US 2013/0211378 A1    Aug. 15, 2013

Related U.S. Application Data

(60) Provisional application No. 61/598,485, filed on Feb. 14, 2012.

(51) Int. Cl.
| | | |
|---|---|---|
| *A61M 37/00* | (2006.01) |
| *A61M 5/168* | (2006.01) |
| *A61M 39/10* | (2006.01) |
| *A61M 5/142* | (2006.01) |
| *A61M 5/148* | (2006.01) |
| *A61M 5/152* | (2006.01) |

(52) U.S. Cl.
CPC ........... *A61M 5/16859* (2013.01); *A61M 5/142* (2013.01); *A61M 5/1483* (2013.01); *A61M 5/1486* (2013.01); *A61M 5/152* (2013.01); *A61M 39/10* (2013.01)

(58) Field of Classification Search
CPC ............ A61M 5/142; A61M 5/16859; A61M 5/15854
USPC ............................................ 604/67, 508, 131
See application file for complete search history.

(56) References Cited

U.S. PATENT DOCUMENTS

| | | |
|---|---|---|
| 2,766,907 A | 10/1956 | Wallace |
| 3,153,414 A | 10/1964 | Beall |
| 3,300,102 A | 1/1967 | Budzich |
| 3,838,794 A | 10/1974 | Cogley |

(Continued)

FOREIGN PATENT DOCUMENTS

| | | |
|---|---|---|
| EP | 0001074 A1 | 3/1979 |
| EP | 77189 B1 | 8/1987 |

(Continued)

OTHER PUBLICATIONS

Kirby et al.; American gastroenterological association medical position statement: guidelines for the use of enteral nutrition; 35 pages; © 1995; retrived from the internet Dec. 10, 2015; (http://www3.us.elsevierhealth.com/gastro/policy/v108n4p1280.html).

(Continued)

*Primary Examiner* — Edelmira Bosques
*Assistant Examiner* — Leah Swanson
(74) *Attorney, Agent, or Firm* — Shay Glenn LLP

(57) ABSTRACT

A pumping device that can be used with currently-available pressure bag infusers is disclosed. The pumping device is hand-held and lightweight. The device is controlled by a microprocessor. Thus constant pressure to the bag is maintained through automatic adjustment of pumping and venting functions. In addition, a novel, new pressure bag infuser and a modified Luer Lock fitting for use with the pumping device are described.

24 Claims, 10 Drawing Sheets

(56) References Cited

U.S. PATENT DOCUMENTS

| | | | |
|---|---|---|---|
| 3,895,741 | A | 7/1975 | Nugent |
| 4,048,994 | A | 9/1977 | Lo |
| 4,507,116 | A | 3/1985 | Leibinsohn |
| 4,551,136 | A | 11/1985 | Mandl |
| 4,684,367 | A | 8/1987 | Schaffer |
| 4,796,788 | A | 1/1989 | Bond |
| 4,857,055 | A | 8/1989 | Wang |
| 5,053,011 | A | 10/1991 | Strobel |
| 5,059,182 | A | 10/1991 | Laing |
| 5,125,900 | A | 6/1992 | Teves |
| 5,207,638 | A | 5/1993 | Choksi |
| 5,257,985 | A | 11/1993 | Puhl |
| 5,497,912 | A | 3/1996 | Hoback |
| 5,505,708 | A | 4/1996 | Atkinson |
| 5,520,638 | A | 5/1996 | O'Quinn et al. |
| 5,720,728 | A | 2/1998 | Ford |
| 5,743,878 | A | 4/1998 | Ross |
| 5,810,202 | A | 9/1998 | Hoback |
| 5,824,000 | A | 10/1998 | Pavlo |
| 5,853,388 | A | 12/1998 | Semel |
| 5,954,696 | A * | 9/1999 | Ryan ............................ 604/141 |
| 6,135,989 | A | 10/2000 | Atad |
| 6,368,314 | B1 * | 4/2002 | Kipfer et al. .................. 604/506 |
| 6,406,458 | B1 | 6/2002 | Tillander |
| 6,558,346 | B1 * | 5/2003 | Yoshioka et al. ............... 604/67 |
| 6,679,840 | B1 * | 1/2004 | Ladd ............................ 600/300 |
| 6,800,069 | B2 | 10/2004 | Lampropoulos |
| 7,182,750 | B2 | 2/2007 | Lampropoulos |
| 7,351,226 | B1 | 4/2008 | Herskowitz |
| 8,211,054 | B2 | 7/2012 | Dewey |
| 2005/0267413 | A1 | 12/2005 | Wang et al. |
| 2008/0312640 | A1 * | 12/2008 | Grant ............................ 604/533 |
| 2010/0179489 | A1 | 7/2010 | Harding |
| 2011/0028937 | A1 | 2/2011 | Powers et al. |
| 2011/0196304 | A1 * | 8/2011 | Kramer et al. ................. 604/151 |
| 2013/0184638 | A1 * | 7/2013 | Scarpaci .................. G01V 8/20 604/28 |

FOREIGN PATENT DOCUMENTS

| | | |
|---|---|---|
| EP | 483759 A1 | 5/1992 |
| EP | 343286 B1 | 8/1992 |
| EP | 1051987 A2 | 11/2000 |
| EP | 1021370 B1 | 10/2002 |
| KR | 10-2002-0036248 A | 5/2002 |
| WO | WO 92/07611 A1 | 5/1992 |
| WO | WO 00/21587 A1 | 4/2000 |

OTHER PUBLICATIONS

Meek; New house officers' knowledge of resuscitation, fluid balance and analgesia; Anaesthesia; 55(11); pp. 1127-1143; Nov. 2000.

Occupational Safety & Health Administration; Controlling occupational exposure to hazardous drugs; SectionVI, Chapter 2; 19 pages; retrieved from the Internet Dec. 10, 2015; (https://www.osha.gov/dts/osta/otm/otm_vi/otm_vi_2.html).

Patel et al.;Comparison of fluid warmer performance during simulated clinical conditions; Canadian Journal of Anaesthesia; 42(7); pp. 636-642; Jul. 1995.

Smiseth et al.; Assessment of pericardial constraint in dogs; Circulation; 71 (1); pp. 158-164; Jan. 1985.

International Search Report and Written Opinion for International Application No. PCT/US2013/026221, Jun. 13, 2013.

* cited by examiner

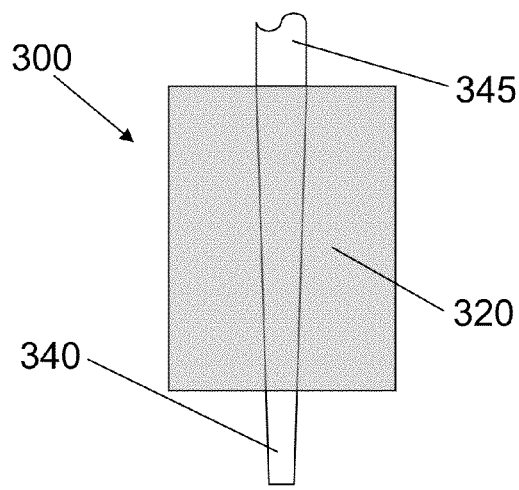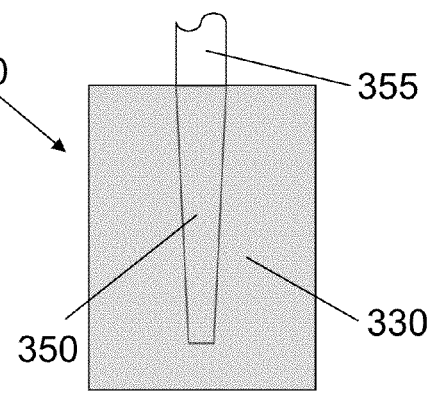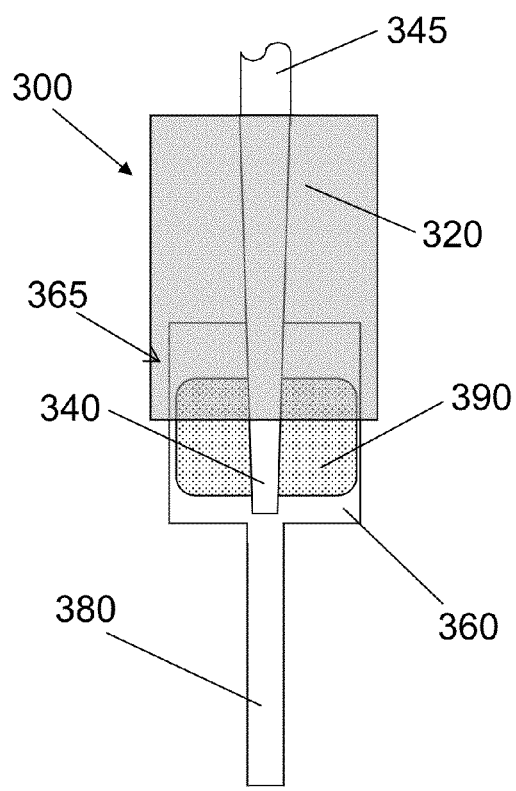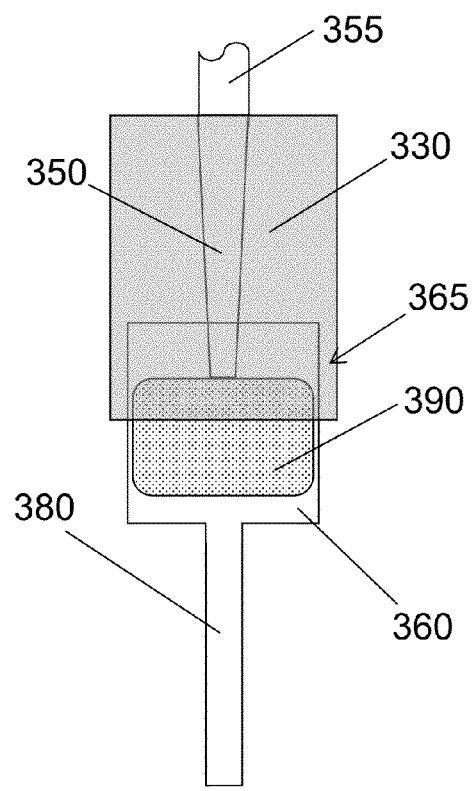
FIG. 3A  FIG. 3C
FIG. 3B  FIG. 3D

PUMP AND MONITOR FOR IV PRESSURE BAG INFUSERS

BACKGROUND OF THE INVENTION

Field of the Invention

This invention relates generally to a pump that can monitor and maintain constant pressure, and, more specifically, to such a pressure bag infuser used for intravenous administration of fluids.

In an emergency situation, a critically ill or injured patient may require rapid administration of fluids or blood products. Clinical conditions for which rapid infusion of intravenous crystalloids and colloids are recommended include cardiac arrest, hypovolemic shock, some endocrine disturbances, distributive shock states, and systemic inflammatory response syndrome. In such cases, IV (intravenous) bags are pressurized to increase the flow rate for the IV fluids therein. Currently, this is done by positioning a pressure bag infuser around the IV bag and inflating the pressure bag to a desired pressure with a hand-held, manual pump. The pressure on the IV bag causes the fluids inside the IV bag to flow into the patient more rapidly than could be achieved with the IV bag and gravity alone.

In emergencies away from the hospital, such as on the battlefield, a blood pressure cuff/pressure infuser is often used to wrap around an IV bag and then inflate to pressurize the bag, causing the fluids inside to outflow more rapidly.

One of the drawbacks to these systems is the requirement of constant monitoring by medical personnel. As fluid flows out of an IV bag, the IV bag decreases in size, thus decreasing the force exerted on the outside of the bag by the pressure infuser, whose position and pressure is fixed, resulting in a decreased infusion rate. Frequently the pressure infuser must be re-pumped manually to maintain constant, rapid IV flow. In a fast-paced, acute care setting or battlefield, critical time is wasted as personnel stop to reassess infusion rates and repeatedly increase pressure in the infuser. Yet, such vigilance is crucial, as failure to assess and maintain the infusion will result in inadequate rapid volume delivery to the patient.

There is a need to automatically maintain pressure on an IV bag to ensure the patient receives the prescribed amount of fluid at the desired rapid rate and to relieve medical personnel of the burden of constant checking. It would be even more useful if the status of the IV infusion could be known simply by glancing at the infusion delivery system from across the room or at a distance.

BRIEF DESCRIPTION OF THE DRAWINGS

The foregoing aspects and others will be readily appreciated by the skilled artisan from the following description of illustrative embodiments when read in conjunction with the accompanying drawings.

FIG. 3A is a schematic illustration of the male portion of a conventional Luer Lock.

FIG. 3B is a schematic illustration that shows how male and female portions of a conventional Luer Lock join together.

FIG. 3C is a schematic illustration of the novel, new male portion of a modified Luer Lock.

FIG. 3D is a schematic illustration that shows how the novel, new male portion and the conventional female portion of a modified Luer Lock join together.

SUMMARY

Figure 1:
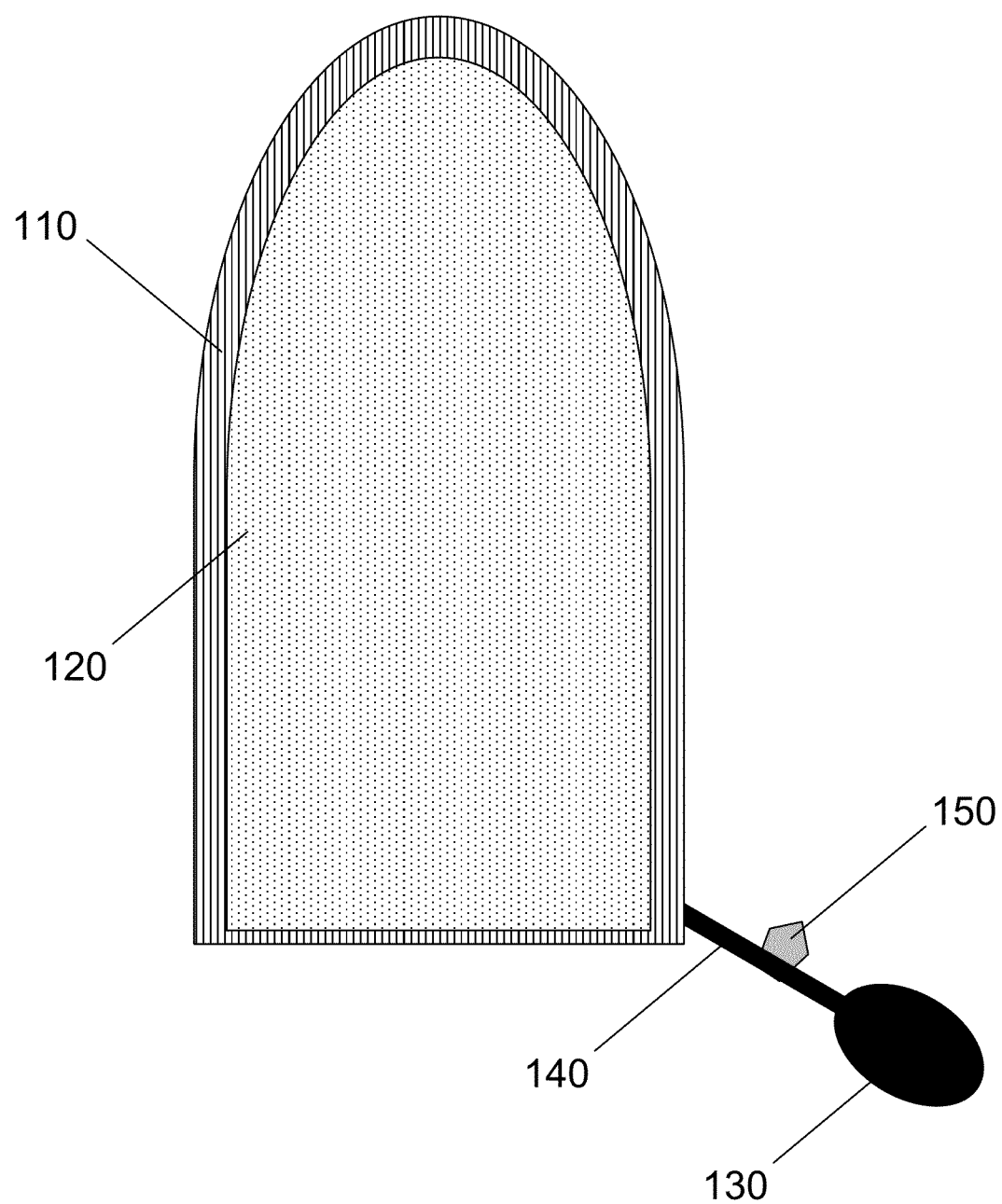
FIG. 1 is a cross-sectional schematic illustration of a pressure infuser 110 for an IV bag as is currently available commercially.

A pumping device is described. The device has a housing that contains at least an electric air pump, a first pressure sensor, an electronic valve, a signaling (light and/or sound) element, a microprocessor in electronic communication with the pump, the first pressure sensor, the signaling element, and the valve. The housing also contains a power source that supplies power to the device and a switch in communication with the power source and optionally, with the microprocessor. In one arrangement, the housing is no more than about 20 cm in length and no more than about 6 cm in width. The housing can be made of metal or plastic.

The pumping device has a coupler through with it can be attached to an outside pressure vessel such as an airtight bag. In one arrangement, the airtight bag is configured to be positioned around an IV bag. In one embodiment of the invention, the coupler is a modified male Luer Lock fitting that is configured to be unable to penetrate through a silicone plug in a female Luer Lock IV fitting.

The microprocessor is configured to receive pressure information from the first pressure sensor and to adjust pump and valve activities to maintain a predetermined pressure on the outside pressure vessel. In one arrangement, the microprocessor also receives pressure information from a second pressure sensor that reads the pressure of the outside environment and can determine the actual pressure on the outside pressure vessel, which is especially useful in situations where the outside pressure is changing.

In one arrangement, the microprocessor sends instructions to the signaling element to signal an alarm when there has been no change in pressure over a predetermined period of time.

The pump device described herein is unique in its ability to interface with most of the existing pressure bag systems on the market. But, even more importantly is the convenience of its user interface that gives it extra value in saving precious time in emergency situations. The microprocessor in the pump can compensate for a large number of pressure-changing situations (for example, changes in atmospheric pressure when patients are flown to medical facilities) to accurately maintain a desired rate of infusion. This can be critically useful not only in hospital and battlefield situations, but also in other emergency medical situations, including critical care transports, flights at altitude, confined space rescue and extreme situations where the IV fluids must actually flow up to the patient. The novel features of the pumping device result not only in elimination of the constant vigilance required by current pressure delivery systems, but could potentially result in better patient outcomes because of extremely fast and accurate IV delivery when time is most critical.

DETAILED DESCRIPTION

The preferred embodiments are illustrated in the context of an IV delivery system. The skilled artisan will readily appreciate, however, that the materials and methods disclosed herein will have application in a number of other contexts where pressure regulation on fluid-filled vessels is desirable, particularly where simple operation is important.

These and other objects and advantages of the present invention will become more fully apparent from the following description taken in conjunction with the accompanying drawings.

Reference will now be made to the drawings wherein like numerals refer to like parts throughout.

The term "pneumatic communication" is used herein to mean that compressed air (or other gas) can flow through those elements which are in said communication. The term "airtight" is used herein to mean preventing the entrance or escape of air or gas under normal infuser bag pressures.

FIG. 1 is a cross-sectional schematic illustration of a pressure infuser 110 that is positioned around an IV bag 120 and is currently available commercially. The infuser bag 110 is a double-walled envelope that fits around the IV fluid bag 120. An inflator bulb 130 is in pneumatic communication with the infuser bag 110 through a hose 140. There is also a fitting 150 on the hose 140, though which fitting, air can be released. Usually, the inflator bulb 130 is used to pump air into the infuser bag 110 by hand so that pressure is applied to the IV bag 120. Often there is a pressure gauge (not shown) near the pump so that it is clear when the desired pressure has been reached. As the amount of fluid in the IV bag 120 decreases, the IV bag becomes smaller, and the pressure applied by the infuser bag 110 is no longer sufficient to maintain the desired IV flow rate. The inflator bulb 130 can be used again to pump additional air into the infuser bag 110 to recreate the original or some other desired pressure on the IV bag 120. As discussed above, the successful use of such a system depends on constant vigilance by medical personnel.

Figure 2:
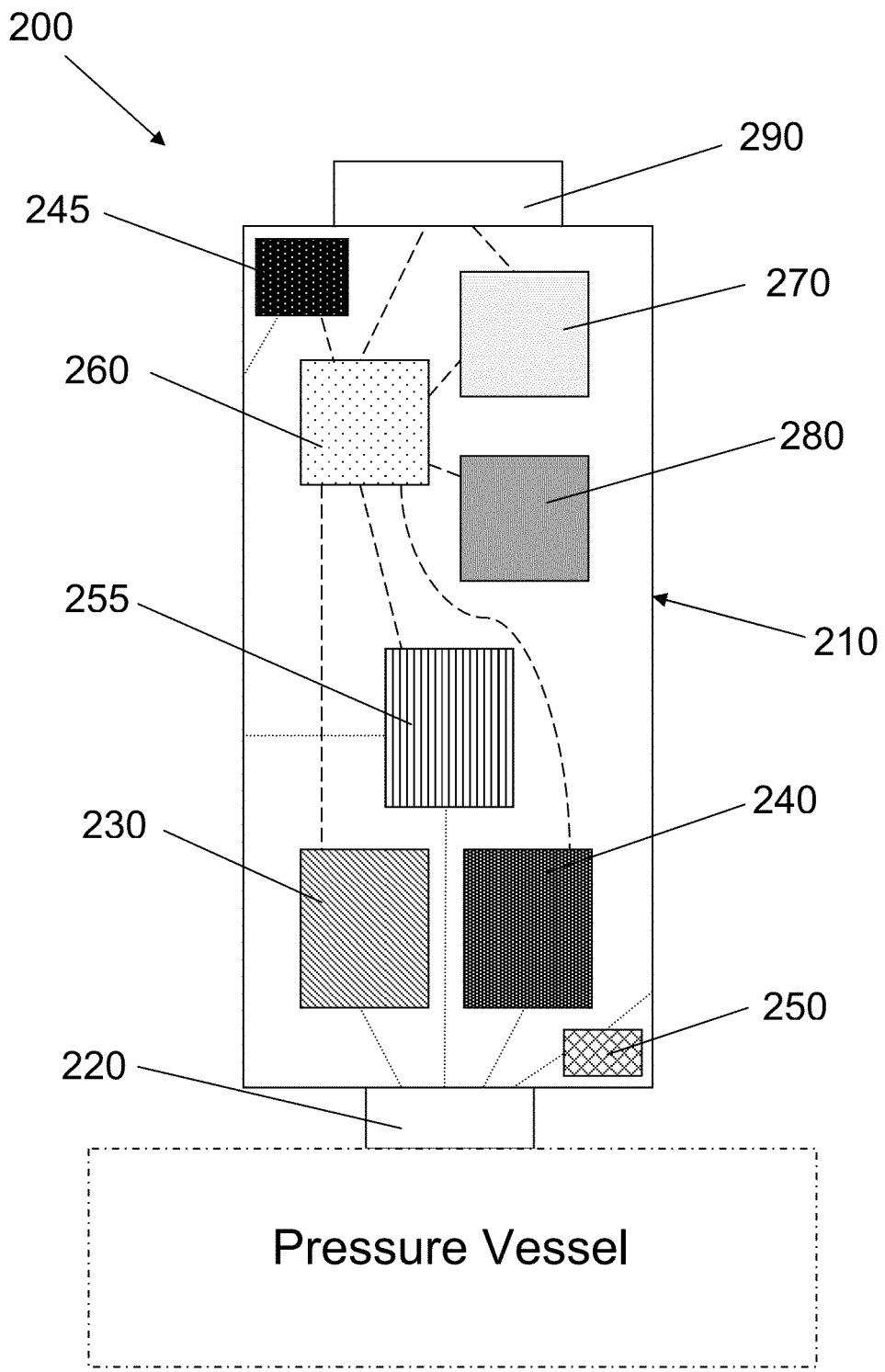
FIG. 2 is a schematic illustration of a novel, new pumping device showing the components therein, according to an embodiment of the invention.

A new, automatic pumping device 200 for managing pressure in pressure vessel, such as an infuser bag or other airtight bag or vessel, according to an embodiment of the invention, is shown in the schematic drawing in FIG. 2. The device 200 has a housing 210. The housing 210 serves to hold the components of the device together. There is a coupler 220 attached to the housing 210. The coupler 220 is configured to attach to an external pressure vessel, such as an infuser bag, with an airtight connection. Much of the discussion of the new device 200 refers to the use of air to pressurize the external pressure vessel. It should be understood that gases other than air can be used in the embodiments of the invention. It should also be understood that the arrangement of elements is schematic only and is not intend to convey any meaning as to their actual placement in the device. Many arrangements of elements within the device are possible.

There is an electric air pump 230 in the housing 210. An example of an appropriate pump 230 is a rotary diaphragm pump paired with an electric motor. The pump 230 is in pneumatic communication with the external pressure vessel. The pump 230 is arranged so that it can pump air (or other gas) through the coupling 220 into the exterior pressure vessel. In one arrangement, there is also an inflator bulb (not shown) in pneumatic communication with the coupling 220 so that air can be pumped into an external pressure vessel by hand if all other systems fail. There is a first pressure sensor 240 in pneumatic communication with the pressure vessel. The first sensor 240 can read the pressure in the exterior pressure vessel. There is a second pressure sensor 245 in pneumatic communication with the outside environment. The second sensor 245 can read the ambient pressure. There is a safety valve 250 with either electronic or mechanical control in pneumatic communication with the pressure vessel. The safety valve 250 is configured to release pressure from the pressure vessel if the pressure vessel reaches unsafe pressures. In an exemplary embodiment, unsafe pressures are those greater than about 300 torr or 40 kilopascals. In some embodiments, there is also a second electronic (or mechanical) valve 255 also in pneumatic communication with the pressure vessel. The second valve 255 closes to maintain air volume in the pressure vessel or opens to release air from the exterior pressure vessel, reducing pressure as needed. Exemplary lines of pneumatic communication are shown as finely dotted lines in FIG. 2.

There is also a microprocessor 260 in the housing 210. The microprocessor 260 receives information from the first pressure sensor 240 and the second pressure sensor 245. The microprocessor 260 determines the actual pressure in the pressure vessel by subtracting the ambient pressure as read by the second sensor 245 from the pressure read by the first sensor 240. The microprocessor 260 uses pre-programmed algorithms to determine instructions to send to the pump 230 and the valve 250 (and/or the second valve 255 in embodiments that include the valve 255), and optionally, the first sensor 240, to adjust their activities. For example, if the actual pressure in the pressure vessel is too low, the microprocessor 260 sends instructions to the pump 230 to begin pumping air into the pressure vessel. When the actual pressure (as determined by the difference between the pressures read by the first sensor 240 and the second sensor 245) in the pressure vessel reaches a desired value, the microprocessor 260 sends instructions to the pump 230 to stop pumping air into the pressure vessel. When the actual pressure (as determined by the difference between the pressures read by the first sensor 240 and the second sensor 245) in the pressure vessel is greater than the desired value, the microprocessor 260 sends instructions to the pump 230 to stop pumping and, optionally, to the second valve 255 to release air from the pressure vessel. In one embodiment of the invention, the first valve 250 will automatically release air from the pressure vessel when the pressure is greater than the desired value, without input from the microprocessor 260.

By using the actual pressure in the pressure vessel in the pre-programmed algorithms, it is possible to change the altitude of the pressure vessel without having to adjust the pressure infuser 110. The pressure infuser adjusts to changes in atmospheric pressure automatically and continuously. This is especially useful if, for example, a patient who is using the pressure infuser is transferred to a helicopter or fixed-wing aircraft for transport.

The frequency with which the microprocessor 260 communicates with the pump 230 and the second valve 255, and optionally, the first sensor 240 can be set in initial programming. Sensing frequency can be anywhere in the range from milliseconds to minutes, or even longer, if desired. In an exemplary embodiment, sensing frequency is several times per second. Thus, the microprocessor 260 can maintain constant pressure in the external pressure vessel through regular adjustment of adding air with the pump 230. Overpressures can be relieved by either the safety valve 250 or through microprocessor 260 instructions to the second valve 255 in embodiments where the second valve 255 is included. In one arrangement, a desired pressure is less than 600 torr or 80 kilopascals (kPa). In another arrangement, a desired pressure is between about 100 and 500 torr (15 and 70 kPa). In yet another arrangement, a desired pressure is between about 255 and 300 torr (35 and 40 kPa). It should be noted that when the pumping device 200 is used for applications other than with IV bags, almost any desired pressure is possible by carefully selecting components of the device 200 which can accommodate the desired pressure.

There is also a power source 280 that provides power for operation of the device. The microprocessor 260 can receive power and optionally send instructions to the power source 280. The microprocessor 260 can also monitor the power level in the power source 280 and alert the user when the power is low. In one arrangement, the power source 280 is a primary battery. In another arrangement, the power source 280 is a secondary battery and has an electrical connection (not shown) accessible from the exterior of the housing 210 so that it can be recharged. In some arrangements, the power source 280 includes both primary and secondary batteries. In yet another arrangement, the power source 280 is a transformer configured to receive external standard outlet power and adjust it for use with the device 200. Other combinations of batteries and outlet power are also possible.

The microprocessor 260 can also send instructions to a signaling element 270 that alerts a user to the status of the pumping device 200. In one arrangement, the microprocessor 255 sends instructions to the signaling element 270 to signal an alarm when there has been no change in pressure in a predetermined period of time. For example, if several minutes (for example, 6 minutes) have gone by without pressure adjustment, it may mean that the pressure infuser bag (external pressure vessel) is squeezing an IV bag that is empty or that has occluded outflow. The signaling element 270 can provide a variety of information on the status of the device 200 to a user. Examples of such status information include, but are not limited to on or off, currently active, currently inactive, inflating, deflating, overpressure, and depleted power state (time to change or recharge battery). The signaling element 270 can signal both status information and alarms to a user using light and/or sound. Examples of light signals include, but are not limited to flashing lights, lights of different colors, and changes in light intensity. In an exemplary embodiment, three different color lights are used; green to signal that everything is operating correctly, red to signal that immediate attention is needed, and yellow to signal that the pump is in a state of transition and should be watched. In one embodiment of the invention, the signaling element 270 can also be activated manually to provide light and act as a flashlight, or to sound an alarm manually.

There is a switch 290 that has at least two positions so that it can turn the device on and off through communication with the power source 280. In one arrangement, the switch 290 is multifunctional with several additional positions with which it can communicate with the microprocessor 260 to activate particular programs for operation. In some embodiments of the invention, the switch 290 can be activated, such as by pressing, to cycle through a variety of functionalities. Examples of possible functionalities include, but are not limited to, any one or more of normal pumping mode, power state mode and flashlight mode. Exemplary lines of electronic communication are shown as dashed lines in FIG. 2.

In one embodiment of the invention, there is also a hand pump in pneumatic communication with the coupler 220 as a backup safety measure.

In one embodiment of the invention, the microprocessor 260 can send a wired or wireless signal to a computer or smart phone to inform the user about the status of the pumping device 200. Information about the performance of the pumping unit 200 can also be used to keep a log so that performance and maintenance issues can be identified in real time.

The housing can be made of metal, plastic, composite, or any other suitable material. It is especially useful if the housing is impact resistant. In one arrangement, the housing 210 is sealed except at the coupler 220 (so that the coupler is open to pneumatic communication with an outside pressure vessel) and at any intake or exhaust ports (not shown). Such ports can be arranged anywhere on the device 200 that is suitable for providing air to the pump 230, contact with the ambient environment for the pressure sensor 245 and air outflow from the valve 250 and optionally the valve 255. It is especially useful if the ports are very small and somewhat shielded to avoid contact with contamination. It is also useful if the housing 210 can be disinfected easily with an antiseptic solution such as Betadine® brand anti-septic solution commercially available from Purdue Products, L.P. of Stamford, Conn.

The pumping device 200 can be especially useful if it is small enough to be easy to carry. In one arrangement, the housing has a size that is no more than about 20 cm in length and no more than about 6 cm in width. In another arrangement, the housing has a size that is no more than about 14 cm in length and no more than about 4.5 cm in width. In yet another arrangement, the housing has a size that is no more than about 9 cm in length and no more than about 2 cm in width.

In one embodiment of the invention, the coupler 220 has a fitting that can form an airtight seal with a coupled fitting on an external pressure vessel and/or a hose leading to an external pressure vessel. In one arrangement, the coupler fitting is a male fitting and the coupled fitting on the external pressure vessel or hose is a female fitting. In another arrangement, the coupler fitting is a female fitting and the coupled fitting on the external pressure vessel or hose is a male fitting. In one arrangement, the coupled fittings are screw-type fittings. In another arrangement, the coupled fittings are pressure-type fittings.

In one arrangement, the fitting is the well-known Luer Lock fitting that is commonly used with IV tubing. An advantage of using a Luer Lock fitting is that it is commonly used and is therefore familiar to medical personnel. It would also be inexpensive to incorporate a Luer Lock into the pressure infuser device. But there can be safety issues in using such a fitting on a pressure infuser as such fittings are used commonly in medical settings for liquid and blood transfer tubing. If the pressure infuser were attached to a Luer Lock fitting on an IV tube that was providing liquids to a patient, it could introduce air into the tubing which would be very dangerous.

Thus, in one embodiment of the invention, the coupler on the pressure infuser has a modified male Luer Lock fitting. Schematic drawings of a conventional IV Luer Lock fitting are shown in FIGS. 3A and 3B and of the modified pressure infuser Luer Lock fitting in FIGS. 3C and 3D. FIG. 3A shows a conventional male Luer Lock fitting 300. It has an outer portion 320 and a hollow, tapered tube 340 connected to a hose or tube 345. FIG. 3B shows the conventional male fitting 300 coupled with a conventional female fitting. The female fitting has an outer portion 360 and a connecting hose 380. The outer portion 320 of the male fitting and the outer portion 360 of the female fitting join together at 365 by twisting. In addition, the female fitting has a silicone plug 390 that keeps the opening to the hose 380 closed when no male fitting is attached. The tapered tube 340 of the male fitting 300 is long enough to move aside or penetrate the silicone plug 390 and make a continuous pathway between the hose or tube 345 and the hose 380.

A modified Luer Lock 310 is shown in FIG. 3C, according to an embodiment of the invention. The modified Luer Lock 310 has an outer portion 330 and a hollow, tapered tube 350 connected to a hose or tube 355. FIG. 3D shows the modified male fitting 310 coupled with a conventional female fitting. The female fitting has an outer portion 360 and a connecting hose 380. The outer portion 330 of the male fitting and the outer portion 360 of the female fitting join together at 365 by twisting. In addition, the female fitting has a silicone plug 390 that keeps the opening to the hose 380 closed when no male fitting is attached. The tapered tube 350 of the modified male fitting 310 is not long enough to move aside or penetrate the silicone plug 390. As shown in FIG. 3D, the tapered tube 350 is just long enough to make contact with, but not penetrate through, the silicone plug 390. In another embodiment, the tapered tube 350 is shorter than shown and does not make contact with the silicon plug 390. In yet another embodiment, the tapered tube 350 is longer than shown and penetrates the silicon plug 390 without pushing all the way through. Thus no a continuous pathway can be made between the hose or tube 355 and the hose 380, ensuring that even if a pressure infuser were mistakenly attached to an IV line providing liquids to a patient, no harm could be done.

In another embodiment of the invention, the coupling (element 220 in FIG. 2) is clearly labeled that it is not for use with IV liquid, but only with air or gas. In another arrangement, the coupling 220 is specifically designed not to be compatible with a Luer Lock fitting, thus ensuring that the pumping device 200 cannot be used accidently to introduce air into a tube that is carrying fluids into a patient.

Figure 4:
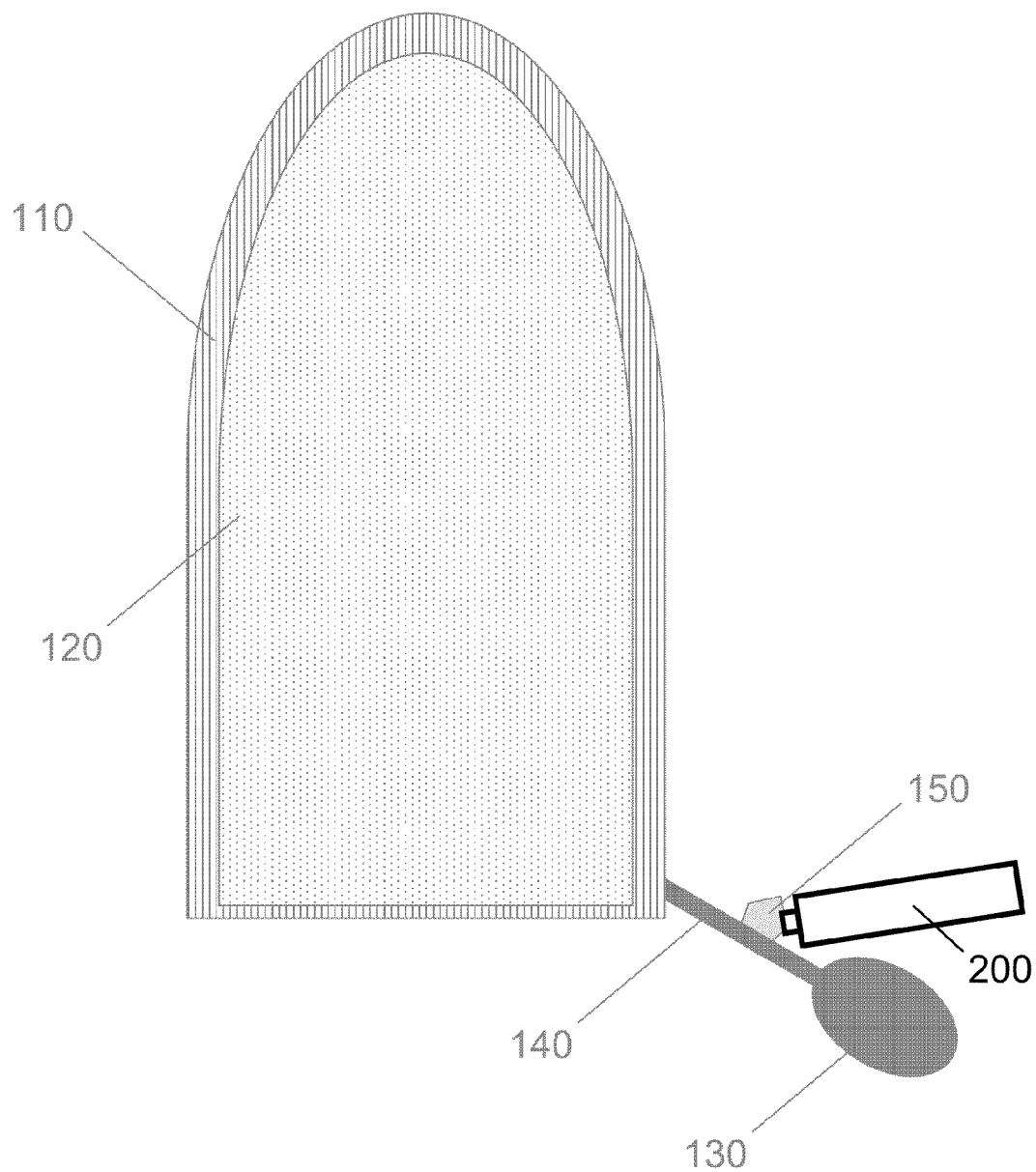
FIG. 4 is a schematic illustration of a new pumping device as used with a pressure infuser around an IV bag, according to an embodiment of the invention.

FIG. 4 shows an example of how the pumping device 200 can be used with the pressure infuser bag of FIG. 1, which is reproduced here in lighter contrast. The pumping device 200 has formed an airtight seal with fitting 150. The inflator bulb 130 is no longer needed to pump up the infuser bag 110. Instead, the pumping device 200 can be activated. It automatically pumps air into the infuser bag 110 until a preset pressure is reached. As the IV bag 120 drains, the pressure decreases. As discussed above with reference to FIG. 2, the pressure sensor 240 in the device 200 can sense the pressure drop, and the microprocessor reads the pressure drop and sends instructions to the pump 230 to pump more air into the infuser bag 110. Thus pressure on the IV bag is maintained at a constant level automatically. A user can see or hear the signaling element 270 to get the status of the pumping device 200. Thus, a standard, commonly-used infuser bag can be made to operate automatically by using the novel pressure device disclosed herein.

Figure 5A:
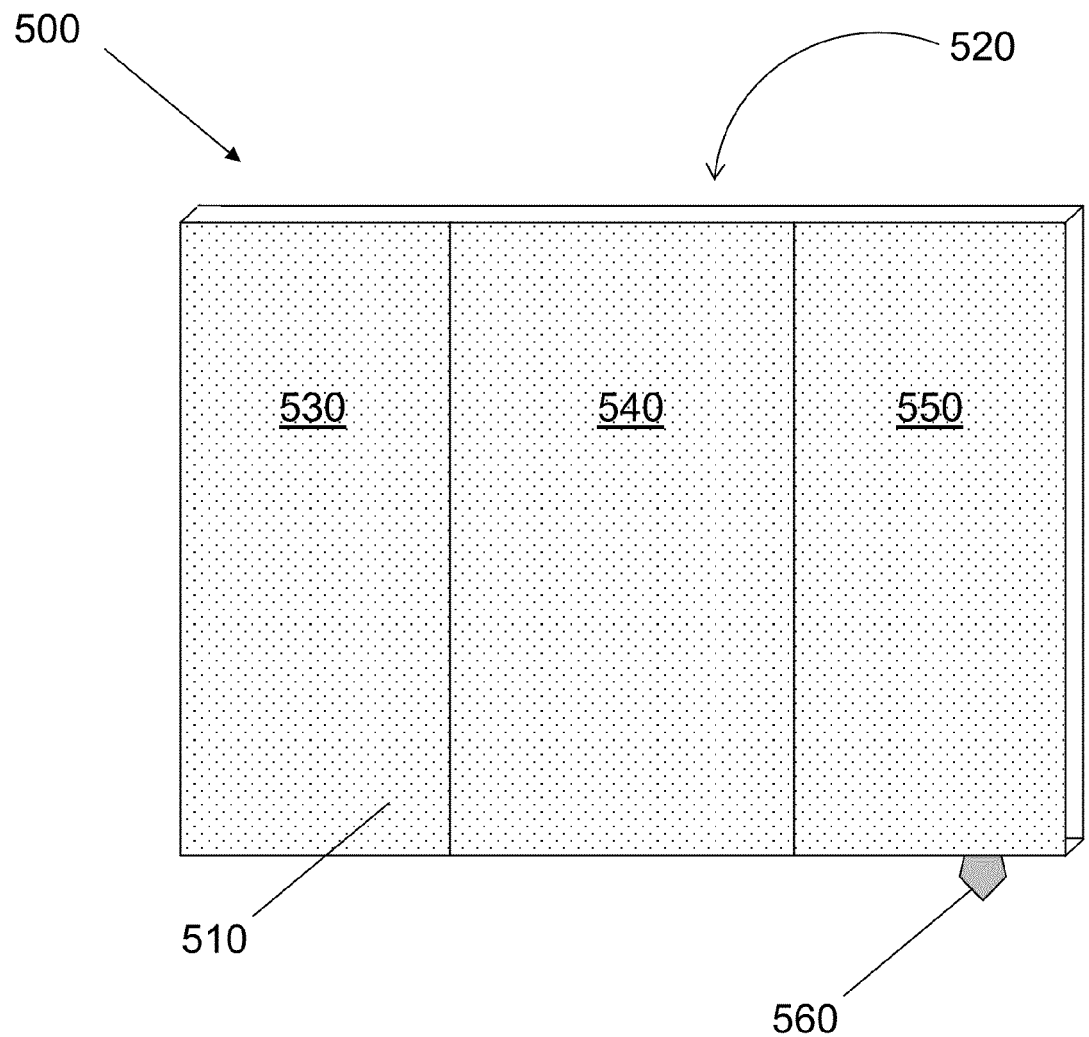
FIGS. 5A and 5B and 6 are schematic illustrations of novel, new infuser bags designed for use with the novel pressure device, according to some embodiments of the invention.
Figure 5B:
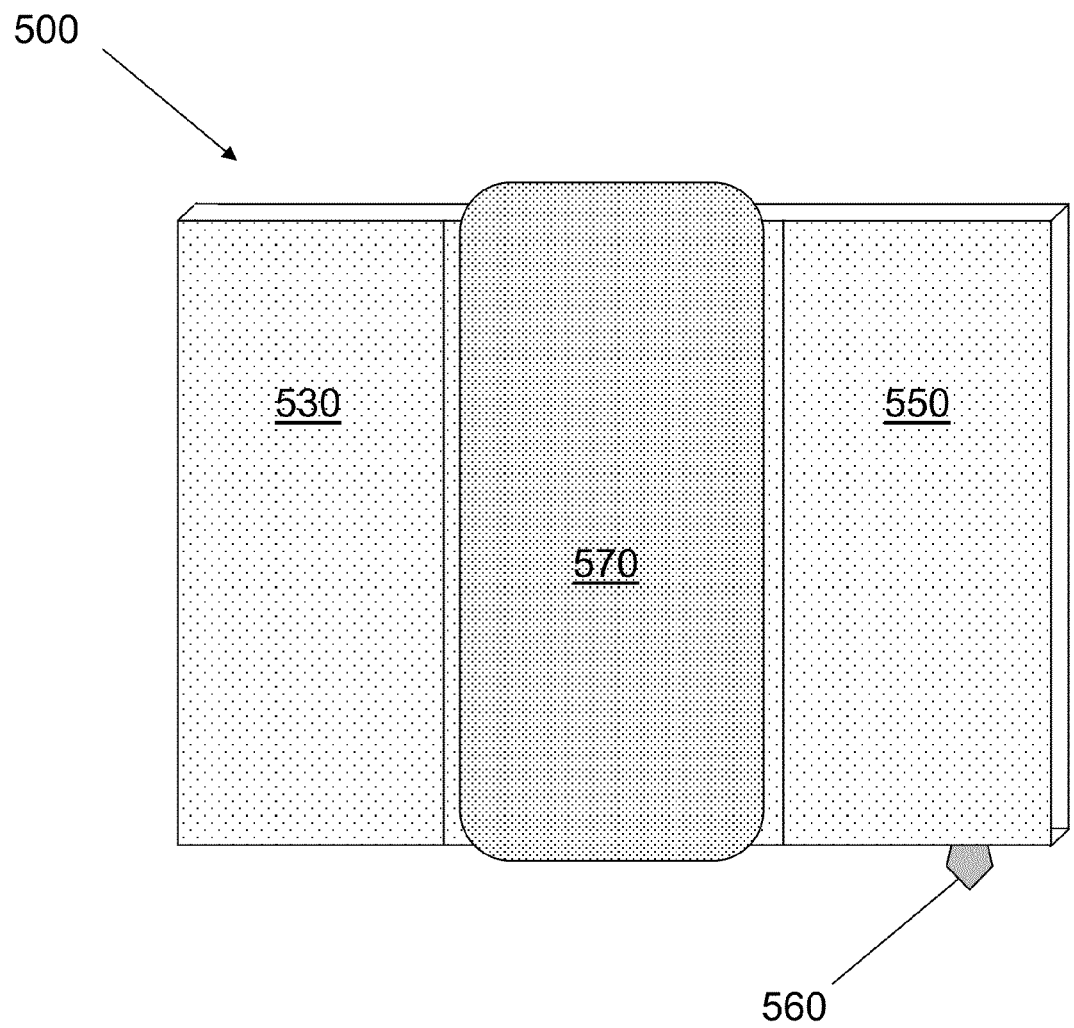

FIG. 5A is a schematic illustration that shows a novel, new infuser bag 500 designed for use with the novel pressure device, according to an embodiment of the invention. The bag 500 has an approximately rectangular shape. The bag 500 has two walls, an inner wall 510 facing the viewer and an outer wall 520 toward the back of the page. The inner wall 510 and the outer wall 520 are sealed together at all four edges to form an airtight space between the walls, which can withstand pressures up to about 80 kPa. In one arrangement, there are no other sealed points of contact between the inner wall 510 and the outer wall 520. In another arrangement, there are several other sealed points of contact between the inner wall 510 and the outer wall 520, while maintaining mostly open space. There is also a fitting 560, though which fitting, air can be introduced into and released from the open space between the inner wall 510 and the outer wall 520. In one arrangement, the inner wall 510 is more pliant than the outer wall 520. In one arrangement, the inner wall 510 is essentially covered with adhesive. In another arrangement, the inner wall 510 is at least partially covered with adhesive. The bag 500 has three sections 530, 540, 550 and is designed to fold around an IV bag or other approximately cylindrically shaped container as shown in FIG. 5B. An IV bag 570 has been placed over and has stuck to section 540. Section 530 can be folded over and stuck onto the IV bag 570. Section 550 can be folded over and stuck onto the outer wall of section 530, thus forming a double-walled pressure vessel, or infusion bag 500 fitted onto the IV bag 570. In another arrangement, Section 550 can be folded over and stuck onto the IV bag 570. Section 530 can be folded over and stuck onto the outer wall of section 550, thus forming a double-walled pressure vessel, or infusion bag 500 fitted onto the IV bag 570. The inventive pumping device described above in FIG. 2 can be joined to form an airtight connection with the fitting 560 so that the infusion bag 500 can be operated automatically as described above.

Figure 6:
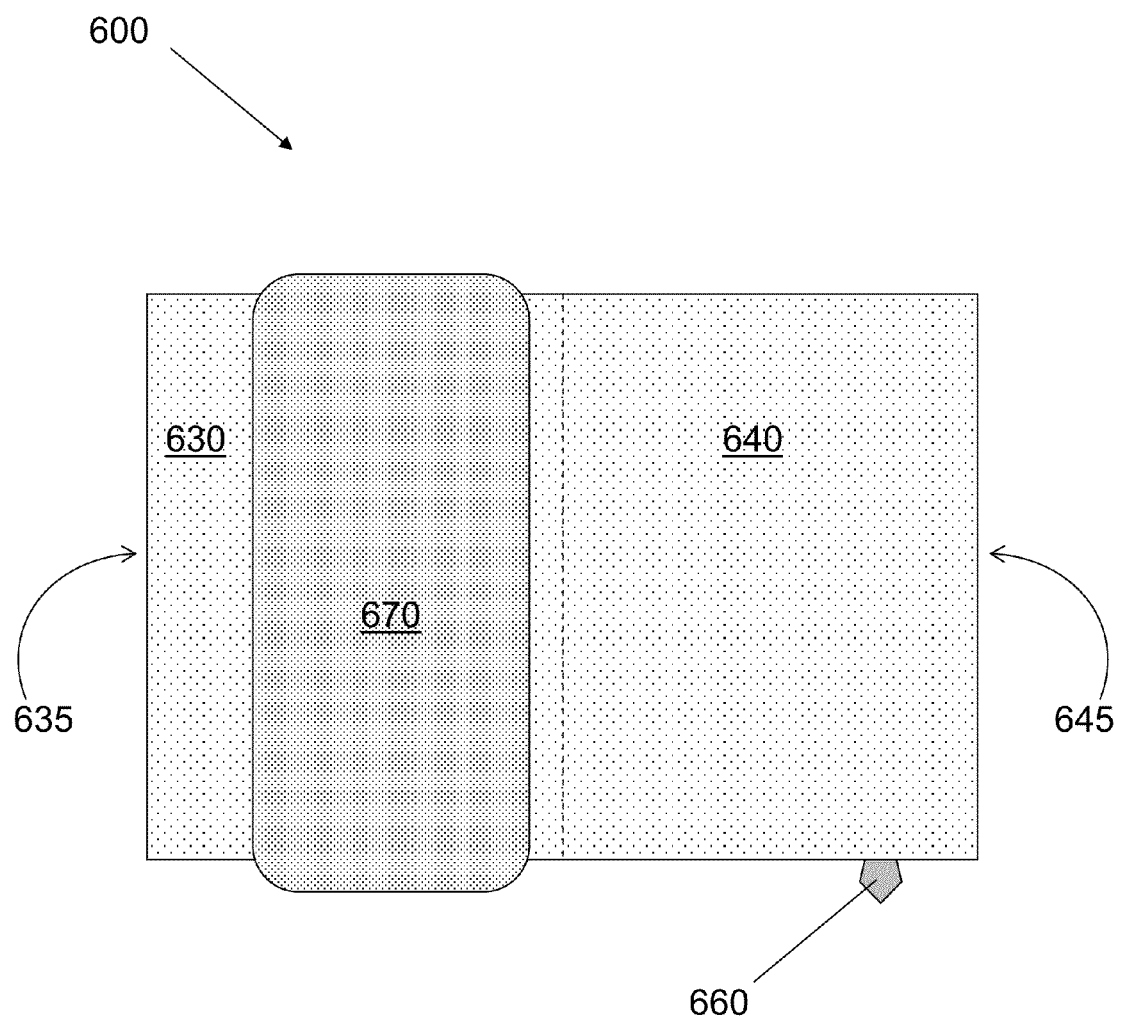

In other embodiments of the invention, other infuser bags with different geometries can be made using the main ideas described in reference to FIGS. 5A and 5B. An exemplary embodiment is shown in FIG. 6. A rectangular, double-walled infuser bag 600 has only two sections 630, 640. Only the inner wall is shown in this figure; the outer wall is not shown. There is also a fitting 660, though which fitting, air can be introduced into and released from the enclosed space between the inner wall and the outer wall. Section 630 has an outer edge 635. Section 640 has an outer edge 645. In one arrangement, the sections 630, 640 are essentially covered with adhesive. In another arrangement, the sections 630, 640 are at least partially covered with adhesive. The IV bag 670 or other approximately cylindrically shaped container can be stuck onto one section, for example onto section 630, and section 640 can be folded over and stuck to the IV bag 670. The edges 635 and 645 are joined together and sealed, thus enclosing the IV bag. The inventive pumping device described above in FIG. 2 can be joined to form an airtight connection with the fitting 660 so that the infusion bag 600 can be operated automatically as described above.

In one embodiment of the invention, the walls of the infuser bags 500, 600 are made of polymers. In one arrangement, the inner wall is more pliant than the outer wall. In one arrangement, the two walls are made of different materials, so that the outer wall is less pliant than the inner wall. In another arrangement, the two walls are made of the same material, but of different thicknesses. The outer wall is thicker than the inner wall. In one arrangement, the infuser bag 500, 600 is transparent or translucent so that the internal IV bag 570, 670 is visible even after the infuser bag has been applied. The outer wall can maintain normal infuser bag pressures up to about 80 kPa with an appropriate margin of safety. In another arrangement, there are instructions printed onto the infuser bag so that the steps used to position it around an IV bag can be understood. In one arrangement, the infuser bags 500, 600 are disposable. In one arrangement, for the infuser bags described in FIGS. 5A, 5B, and 6, there are instructions visible on the outer wall or the inner wall of the infuser bag. The instructions describe how the infuser bag can be joined into an IV bag or other approximately cylindrically shape container.

Figure 7:
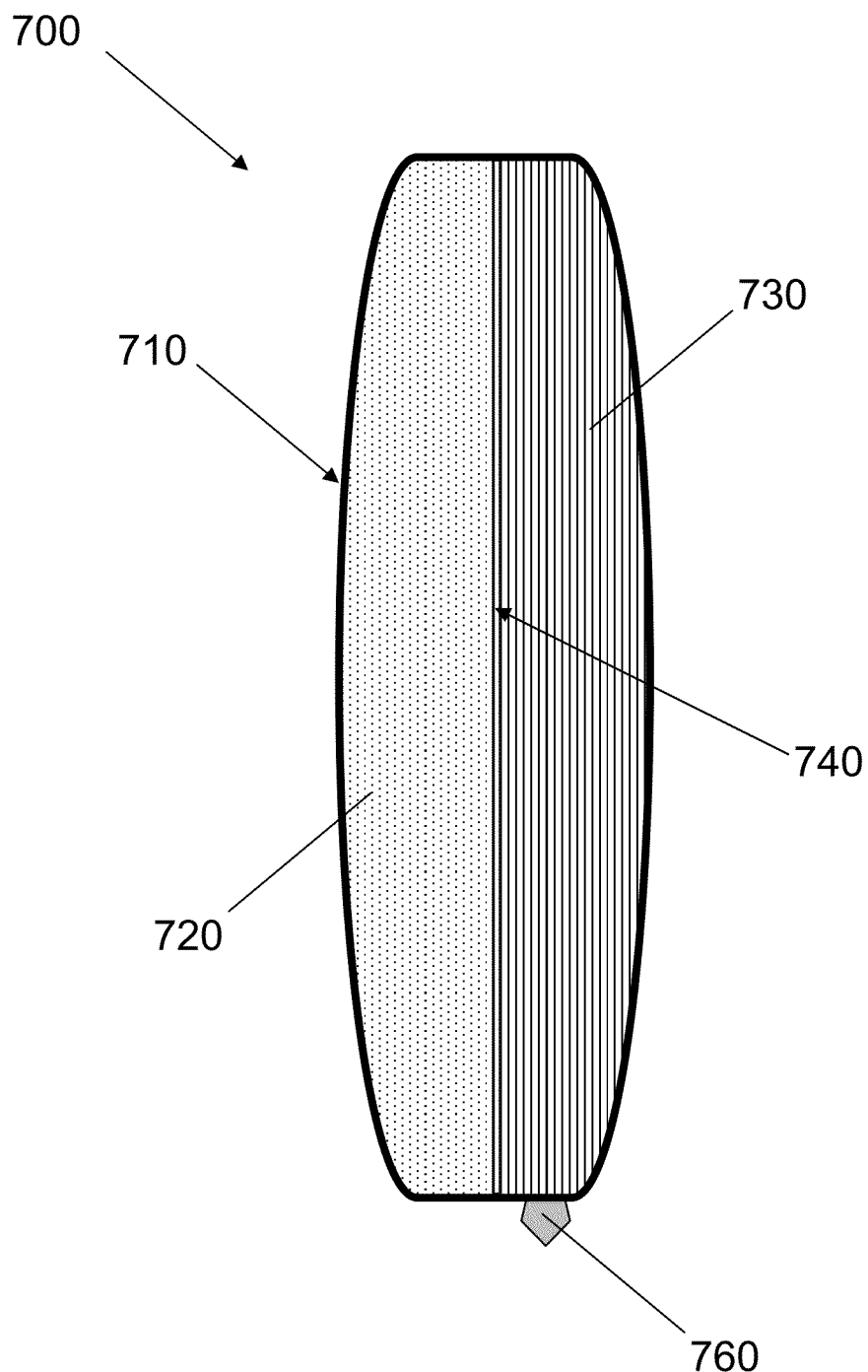
FIGS. 7, 8 and 9 are schematic drawings of novel, new pressurized IV bags for use with the inventive pump described above, according to some embodiments of the invention.

FIG. 7 is a schematic drawing of a novel, new pressurized IV bag 700 for use with the inventive pump described above, according to an embodiment of the invention. Within an outer enclosure 710, the IV bag 700 contains two separate spaces; an IV fluid space 720 and an air pressure space 730. The two spaces are adjacent to one another and are separated by an airtight membrane 740. The outer enclosure 710 can maintain normal infuser bag pressures up to about 80 kPa with an appropriate margin of safety. There is also a fitting 760 in pneumatic communication with space 730, though which fitting, air can be introduced into and released from the air pressure space 730. Instead of using a separate pressure bag infuser, air can be pumped into the air space 730 to pressurize the fluid in the IV fluid space. The inventive pumping device described above in FIG. 2 can be joined to form an airtight connection with the fitting 760 so that the pressurized IV bag can be operated automatically as described above.

Figure 8:
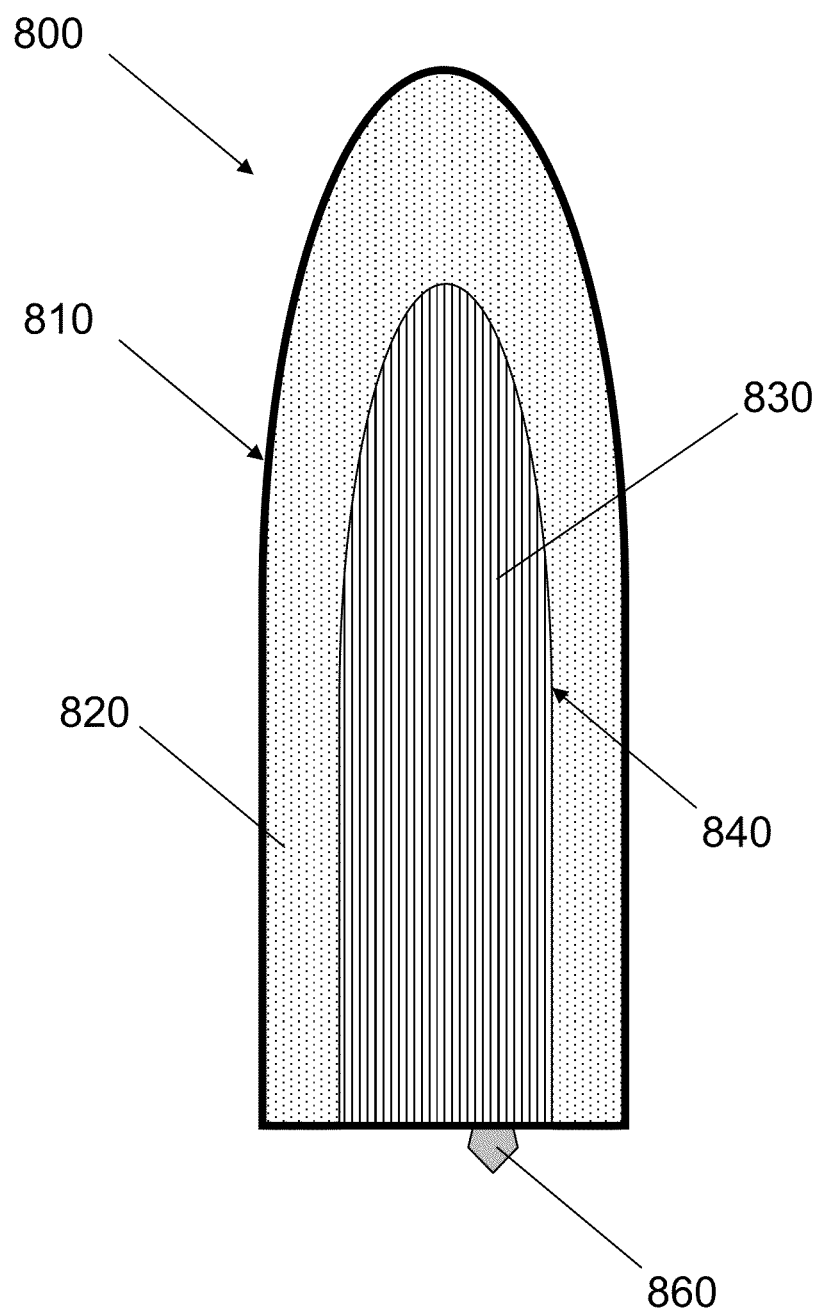

FIG. 8 is a schematic drawing of a novel, new pressurized IV bag 800 for use with the inventive pump described above, according to another embodiment of the invention. Within an outer enclosure 810, the IV bag 800 contains two separate spaces; an IV fluid space 820 and an air pressure space 830. The air pressure space 830 is enclosed within the IV fluid space 820 and the spaces are separated by an airtight membrane 840. The outer enclosure 810 can maintain normal infuser bag pressures up to about 80 kPa with an appropriate margin of safety. There is also a fitting 860 in pneumatic communication with the air pressure space 830, though which fitting, air can be introduced into and released from the air pressure space 830. Instead of using a separate pressure bag infuser, air can be pumped into the air pressure space 830 to pressurize the fluid in the IV fluid space 820. The inventive pumping device described above in FIG. 2 can be joined to form an airtight connection with the fitting 860 so that the pressurized IV bag can be operated automatically as described above.

Figure 9:
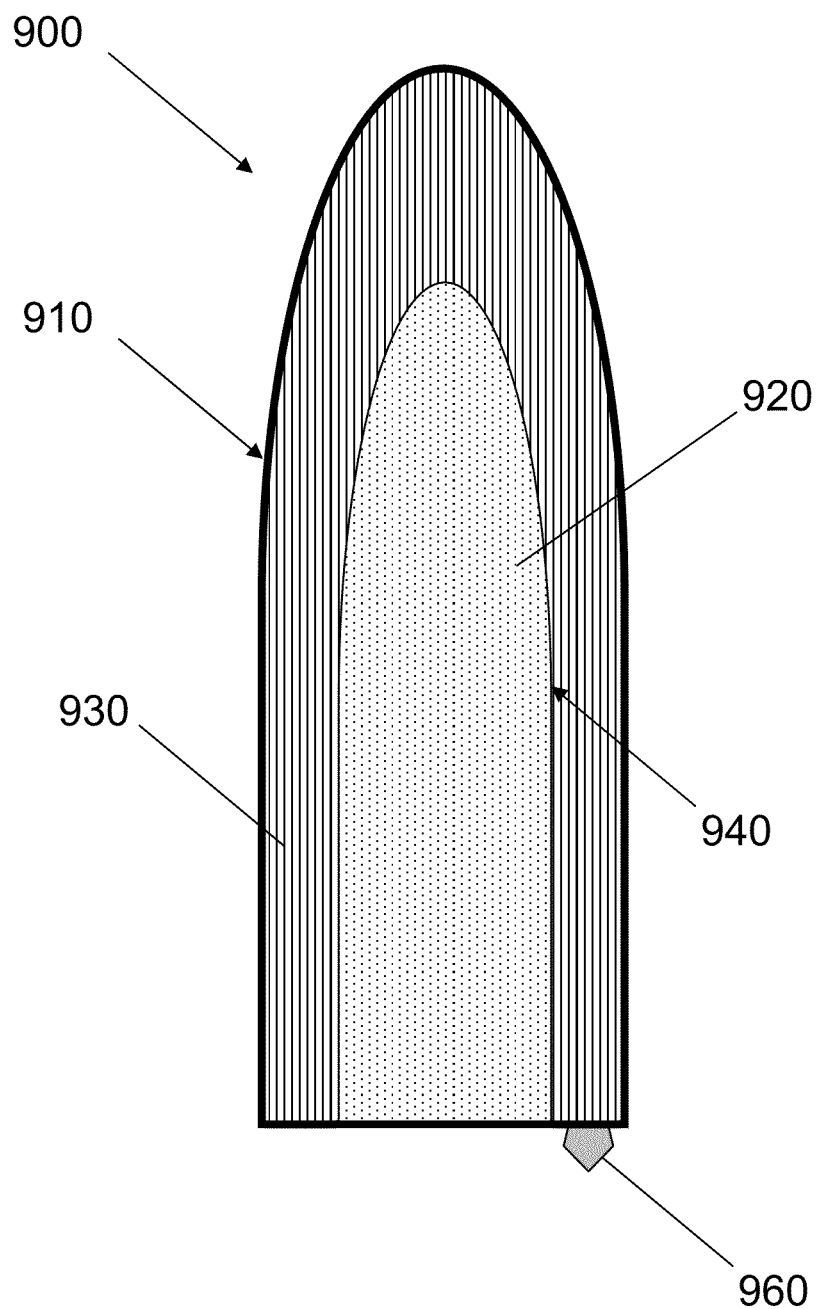

FIG. 9 is a schematic drawing of a novel, new pressurized IV bag 900 for use with the inventive pump described above, according to another embodiment of the invention. Within an outer enclosure 910, the IV bag 900 contains two separate spaces; an IV fluid space 920 and an air pressure space 930. The IV fluid space 920 is enclosed within the air pressure space 930 and the spaces are separated by an airtight membrane 940. The outer enclosure 910 can maintain normal infuser bag pressures up to about 80 kPa with an appropriate margin of safety. There is also a fitting 960 in pneumatic communication with the air pressure space 930, though which fitting, air can be introduced into and released from the air pressure space 930. Instead of using a separate pressure bag infuser, air can be pumped into the air pressure space 930 to pressurize the fluid in the IV fluid space. The inventive pumping device described above in FIG. 2 can be joined to form an airtight connection with the fitting 960 so that the pressurized IV bag can be operated automatically as described above.

The pump device described herein is unique in its ability to interface with most of the existing pressure bag systems on the market. But, even more importantly is the convenience of its user interface that gives it extra value in saving precious time in emergency situations. The microprocessor in the pump can compensate for a large number of pressure-changing situations (for example, changes in atmospheric pressure when patients are flown to medical facilities) to accurately maintain a desired rate of infusion. This can be critically useful not only in hospital and battlefield situations, but also in other emergency medical situations, including critical care transports, flights at altitude, confined space rescue and extreme situations where the IV fluids must actually flow up to the patient. The novel features of the pumping device result not only in elimination of the constant vigilance required by current pressure delivery systems, but could potentially result in better patient outcomes because of extremely fast and accurate IV delivery when time is most critical.

This invention has been described herein in considerable detail to provide those skilled in the art with information relevant to apply the novel principles and to construct and use such specialized components as are required. However, it is to be understood that the invention can be carried out by different equipment, materials and devices, and that various modifications, both as to the equipment and operating procedures, can be accomplished without departing from the scope of the invention itself.

I claim:

1. A rapid infusion pumping device, comprising:
a housing;
a coupler attached to the housing, the coupler configured to attach with an airtight connection to a pressure vessel;
an electric air pump in the housing, the pump in pneumatic communication with the pressure vessel via the coupler;
a first pressure sensor in the housing and in pneumatic communication with the pressure vessel;
a second pressure sensor in the housing configured to measure an atmospheric pressure and in pneumatic communication with an atmosphere outside of the pressure vessel;
an electronic valve within the housing and in pneumatic communication with the pressure vessel;
a signaling element within the housing and configured to be perceptible while observing the housing;
a microprocessor within the housing and containing preprogrammed algorithms for the operation of the rapid infusion pumping device, the microprocessor in electronic communication with the pump, the first pressure sensor, the second pressure sensor, the valve, and the signaling element wherein the microprocessor receives pressure information from the first pressure sensor and the second pressure sensor and operates the electric air pump and the electronic valve to maintain a predetermined pressure within the pressure vessel; and
a power source within the housing configured for supplying power to the device via the microprocessor.

2. The pumping device of claim 1 wherein the housing has a size that is no more than about 20 cm in length and no more than about 6 cm in width.

3. The pumping device of claim 1 wherein the housing comprises metal or plastic.

4. The pumping device of claim 1 wherein the housing is sealed except at the coupler and at intake or exhaust ports.

5. The pumping device of claim 1 wherein the pressure vessel is an airtight bag.

6. The pumping device of claim 5 wherein the airtight bag is configured to be positioned around an IV bag.

7. The pumping device of claim 5 wherein the airtight bag is an integral part of an IV bag.

8. The pumping device of claim 1 wherein the coupler comprises a modified male Luer Lock fitting that is configured to be unable to penetrate through a silicone plug in a female Luer Lock fitting when the male fitting and the female fitting are attached securely.

9. The pumping device of claim 1 wherein the microprocessor receives pressure information from the first pressure sensor and the second pressure sensor, and the microprocessor adjusts pump and valve activities to maintain a predetermined pressure.

10. The pumping device of claim 1 wherein the signaling element signals through light, sound, or a combination thereof.

11. The pumping device of claim 1 wherein the microprocessor sends instructions to the signaling element to signal an alarm when there has been no change in pressure over a predetermined period of time.

12. The pumping device of claim 1 wherein the signaling element indicates the status of the device wherein the status is one or more selected from the group consisting of on, off, currently active, currently inactive, inflating, deflating, overpressure, and depleted power state.

13. The pumping device of claim 1 further comprising a multifunctional electronic switch that when activated cycles the pumping device through a series of different function modes.

14. The pumping device of claim 1 further comprising a hand pump in pneumatic communication with the coupler.

15. The pumping device of claim 1 wherein the pressure vessel is a double walled envelope.

16. The pumping device of claim 1 wherein the pressure vessel is formed from an infuser bag having a plurality of sections, the sections are arranged so as to at least partially encircle a fluid infusion bag and are joined by an adhesive section on one of the plurality of sections.

17. The pumping device of claim 1 wherein the signaling element provides a series of different signals responsive to a status indication of the pumping device determined by the microprocessor.

18. The pumping device of claim 17 wherein the signaling device provides signals to indicate the operational states of a proper operation state, an operation state that requires immediate attention and an transitional state requiring further monitoring.

19. A method of performing a rapid fluid infusion, comprising:

Operating a multifunction switch to initiate a rapid fluid infusion sequence;

Detecting and providing to a microprocessor a first pressure of a pressure vessel containing a fluid bag having a liquid to be delivered to a patient using a rapid fluid infusion;

Detecting and sending to the microprocessor an atmospheric pressure of an environment external to the pressure vessel;

Operating a pump under the control of the microprocessor to maintain the pressure in the pressure vessel within a predetermined pressure range; and Delivering the fluid within the fluid bag to a patient.

20. The method of claim 19 wherein the predetermined pressure range is between 100 Torr and 500 Torr.

21. The method of claim 20 wherein the predetermined pressure range is between 255 Torr and 300 Torr.

22. The method of claim 19 further comprising actuating a safety valve under the control of the microcontroller where the microprocessor determines that the first pressure is greater than 300 Torr.

23. The method of claim 19 further comprising operating the microprocessor to compare the first pressure and the second pressure to determine a change in ambient pressure of the pressure vessel.

24. The method of claim 19 further comprising detecting a change in ambient pressure of the pressure vessel by operating the microprocessor to compare the first pressure and the second pressure and operating the pump in response to the detected change in the ambient pressure.

* * * * *